United States Patent [19]

Signorino

[11] Patent Number: 5,591,455
[45] Date of Patent: Jan. 7, 1997

[54] WET POWDER FILM-FORMING COMPOSITIONS

[75] Inventor: Charles A. Signorino, King of Prussia, Pa.

[73] Assignee: Warner-Jenkinson Company, Inc., St. Louis, Mo.

[21] Appl. No.: 382,283

[22] Filed: Feb. 1, 1995

Related U.S. Application Data

[60] Division of Ser. No. 73,795, Jul. 27, 1993, which is a continuation-in-part of Ser. No. 630,815, Dec. 20, 1990, abandoned.

[51] Int. Cl.$^6$ .............................. A61K 9/16; A61K 9/50
[52] U.S. Cl. .................... 424/490; 424/489; 424/488; 424/465
[58] Field of Search ....................... 424/490, 489, 424/488, 34, 465; 426/104

[56] References Cited

U.S. PATENT DOCUMENTS

| | | | |
|---|---|---|---|
| 4,543,370 | 9/1985 | Porter et al. | 424/34 |
| 4,994,285 | 2/1991 | Hisano et al. | 426/104 |
| 5,126,145 | 6/1992 | Evenstad et al. | 424/465 |

Primary Examiner—Thurman K. Page
Assistant Examiner—William E. Benston, Jr.
Attorney, Agent, or Firm—Whyte Hirschboeck Dudek S.C.

[57] ABSTRACT

An improved wet powder, edible, film-forming composition for use in coating tablets and capsules consists essentially of powdered pigment particles, a film-forming, water soluble or water-dispersible, edible polymer and up to approximately 30% by weight of water. Such compositions are formed by blending the pigment particles and the polymer and applying the water onto the pigment-polymer blend in atomized form. Similar wet powder, edible, clear, film-forming compositions for use in coating tablets and capsules with a clear coating consist essentially of a film-forming, water soluble or water-dispersible, clear, edible polymer and up to approximately 30% by weight of water and are formed by applying the water onto the polymer in atomized form. The application of water in this manner preconditions the polymer and permits the preparation of smooth stable coating suspensions upon dilution with additional water and without the formation of fish eyes.

14 Claims, No Drawings

WET POWDER FILM-FORMING COMPOSITIONS

CROSS-REFERENCE TO RELATED APPLICATION

This is a division of application Ser. No. 08/073,795, filed Jul. 27, 1993 which is a continuation-in-part of application Ser. No. 630,815, filed Dec. 20, 1990.

BACKGROUND OF THE INVENTION

This invention relates to film-forming or film coating compositions for use in the film coating of pharmaceutical tablets and the like and, more particularly, to such compositions in the form of wet powder blends or wet powder, clear, film-forming compositions.

Signorino U.S. Pat. No. 3,981,984 discloses edible concentrated pigment suspension in which pigments are suspended in non-aqueous solvents. Such pigment suspensions are shipped, for example, to pharmaceutical manufacturers who mix them with polymer solutions to form coating suspensions used for coating tablets and the like. Each of the pigment suspensions, polymer solutions and coating suspensions formed therefrom are in a non-aqueous solvent.

Porter et al. U.S. Pat. No. 4,543,370 discloses a dry edible film coating composition for use in pharmaceuticals, confectionary and food which comprises a mixture including pigment particles, polymer particles, a polymer plasticizer such as polyethylene glycol 400 and, advantageously, a surfactant such as dioctyl sodium sulfosuccinate. According to the patentees, such a film coating composition responds to a long standing desire to provide a dry edible film coating composition which can be constituted with solvent by the customer, that eliminates the problem of shipping of pigment dispersions containing aqueous or non-aqueous solvents, and also makes shipping less expensive by eliminating the weight of the solvents. In U.S. Pat. No. 4,543,370 it is stated to be known in the prior art to mix a dry polymer powder with pigment particles and to grind the mixture to obtain a dry polymer-pigment mixture which is then ground into a fine powder mixture. However, as further stated in this patent, when this fine polymer-pigment mixture is stirred into water and dispersed, the polymer makes lumps and fish eyes because it agglomerates and the resultant dispersion is not uniform. When this polymer-pigment dispersion is used as a coating dispersion and is coated onto tablets and the like, unless the dispersion is left to solvate for a considerable period of time like overnight, the coating is lumpy and not uniform.

The dry coating compositions of U.S. Pat. No. 4,543,370 are stated to be useful within an hour of being made up and not to require an overnight waiting period as was required by prior art aqueous and non-aqueous systems.

Heinze U.S. Pat. No. 4,636,261 discloses dry mixtures of powdered edible pigment particles and a dispersing agent which prevents agglomeration and facilitates dispersion into solution. The dispersing agent may be the salt of an organic compound containing one to four carboxylic acid groups or a salt of phosphoric acid.

In the preparation of clear film coating compositions for coating aspirin tablets and the like, it has heretofore been the practice to dissolve or disperse a polymer such as hydroxypropylmethyl cellulose in water and then wait for a period of 18 hours or so before applying the resulting polymer solution or dispersion to tablets or the like. Such a waiting period has been deemed necessary in order to rid the solution or dispersion of fish eyes and allow water to penetrate into or hydrate the polymer gel particles (fish eyes) which form upon dissolving or dispersing the polymer in water. While pre-conditioned or surface-treated polymers are available, it is necessary to add a base material to such polymers in order to allow the polymers to become hydrated and dissolve or disperse in water.

There remains a need for further improvements in film coating compositions with regard to their ability to disperse color in the coating of tablets, capsules and the like and their usefulness for this purpose upon preparation or within a short time thereafter.

SUMMARY OF THE INVENTION

Among the objects of the present invention may be noted the provision of film-forming compositions useful in coating tablets, capsules and the like which are produced in the form of wet powder blends; the provision of clear film-forming compositions for use in coating tablets and capsules with a clear coating; the provision of such compositions which are capable of forming stable suspensions for coating tablets, capsules or the like upon dilution with additional water; the provision of compositions of this type which can be used for coating tablets and capsules shortly after being combined with additional water and a plasticizer; and the provision of methods of making such film-forming compositions. Other objects and features will be in part apparent and in part pointed out hereinafter.

Briefly, the present invention is directed to a wet powder, edible, film-forming composition for use in coating tablets, capsules and the like which consists essentially of powdered pigment particles, a film-forming, water-soluble or water-dispersible, edible polymer and between approximately 1% and approximately 30% by weight of water, the composition being formed by blending the pigment particles and polymer and applying the water onto the pigment-polymer blend in atomized form and the composition being capable of forming a stable suspension upon dilution with additional water. Preferably, the composition also contains a dispersing agent such as an alkali metal or ammonium salt of ethylene diamine tetraacetic acid which lowers the surface tension of water in the composition.

The invention is also directed to a method of making a wet powder, edible, film-forming composition of the type described above for use in coating tablets, capsules and the like which comprises (a) blending powdered pigment particles and a film-forming, water-soluble or water-dispersible edible polymer; and (b) applying water or an aqueous solution of the above-mentioned dispersing agent onto the pigment-polymer blend in atomized form, the composition containing between approximately 1% and approximately 30% by weight of water.

The invention, in another embodiment, is further directed to a wet powder, edible, clear, film-forming composition for use in coating tablets, capsules and the like with a clear coating consisting essentially of a clear, film-forming, water-soluble or water-dispersible, edible polymer and between approximately 1% and approximately 30% by weight of water, the compositions being formed by applying water onto the polymer in atomized form and the composition being capable of forming a stable suspension upon dilution with additional water without the formation of fish eyes. The composition of this embodiment of the invention preferably also contains a dispersing agent of the aforementioned type, and the invention further encompasses a method of making a clear, film-forming composition of this embodiment.

DESCRIPTION OF THE PREFERRED EMBODIMENTS

In accordance with the present invention, it has now been unexpectedly found that useful wet powder, edible, film-forming compositions for coating tablets, capsules and the like may be formulated by blending powdered pigment particles with a film-forming, water-soluble or water-dispersible, edible polymer and applying water onto the pigment-polymer blend in atomized form. When formulated in this manner, the resulting film-forming compositions have been found capable of tolerating up to approximately 30% by weight water while yet remaining capable of forming a stable suspension upon dilution with additional water. Also, the film-forming compositions prepared in accordance with the present invention and containing between approximately 1% and approximately 30% by weight of water do not lump up or contain fish eyes and, when combined with additional water and a plasticizer provide a smooth, uniform coating for pharmaceutical tablets, capsules and the like. Optionally, but preferably, the film-forming compositions of the invention also contain a dispersing agent constituted by an acid salt which lowers the surface tension of the water in the composition and which in turn lowers the viscosity of the final coating suspension to thereby provide improved and smoother coatings for tablets and the like.

It is believed that the addition or application of water onto the pigment-polymer blend in atomized form in accordance with the invention advantageously preconditions the polymer and avoids clumping or the formation of fish eyes when the compositions of the invention are added to water to form coating suspensions. Thus, by applying the water in atomized form, the water becomes uniformly distributed over or to all polymer particles, the pigment particles adhere to the polymer particles and the polymer is preconditioned so that hydration of the polymer is expedited when the pigment-polymer blend is dispersed in water to form a coating suspension. Accordingly, the present invention achieves the advantageous preconditioning of the blend of pigment and polymer causing the blend to readily disperse and dissolve in water in forming the desired coating suspension without deleterious lumping or agglomeration. Moreover, through the present invention, it becomes possible to prepare smooth coating suspensions which can be used immediately or within 30 minutes for the coating of tablets or the like.

In the practice of the present invention, powdered pigment particles are first blended or admixed with a film-forming, water-soluble or water-dispersible, edible polymer. Water or an aqueous solution of a dispersing agent which lowers the surface tension of water is then applied onto the pigment-polymer blend in atomized form to produce a film-forming composition containing between approximately 1% and approximately 30% by weight of water. For use as the powdered pigment component of the compositions of the invention, any FDA approved edible natural or synthetic colorant may be employed. Useful pigments include, but are not limited to, FD&C and D&C dyes, FD&C and D&C lakes, titanium dioxide, iron oxides, talc, alumina, silica and natural colorants. Typically, the powdered pigment particles may be constituted by a combination of a lake and titanium dioxide or iron oxide. The particle size of the powdered pigment particles is not critical, but the finer the particle size, the better the results achieved through the present invention. The particle size of commercially available pigments known to those in the art renders them satisfactory for use in the compositions of the invention.

In order to be useful in the invention, the film-forming, edible polymer component must be water-soluble or water-dispersible. Useful polymers of this type include methyl cellulose, hydroxypropylmethyl cellulose, hydroxypropyl cellulose, polyvinyl pyrrolidone, maltodextrin, polydextrose, modified starches (such as "Purity Gum 59" marketed by National Starch) and natural gums such as gum tragacanth, gum acacia and xanthan gums, with hydroxypropylmethyl cellulose being the preferred polymer. Mixtures of such polymers may also be used. It is preferred that the polymer be in powdered form, but the particular particle size of the polymer is not critical in the practice of the invention.

After the powdered pigment and polymer have been blended until uniform, the desired amount of water per se or in the form of an aqueous solution of a dispersing agent is added with intense mixing so that the water or aqueous solution of the dispersing agent is applied to the pigment-polymer blend in atomized form. This can be accomplished, for example, by blending the powdered pigment and polymer in a PK Blender or a Littleford FM 130 Blender and adding the water or aqueous solution of dispersing agent with intense mixing by fine atomization into the blender chamber where the powdered pigment and polymer are being mixed. Preferably, the water or aqueous solution is added slowly and the resulting water-containing blend or composition is mixed intensely after addition of the water.

It has been found that film-forming compositions prepared in this manner may contain up to approximately 30% by weight of water and yet remain capable of forming a stable suspension useful for coating tablets and the like upon dilution with additional water. It should be noted that where FD&C lakes are employed as pigments, they may contain up to 15% by weight of water and that the polymer component may likewise contain up to 4% to 6% by weight of water. The water added through the practice of this invention is additional water over and above that contained in the pigment and polymer components and, as stated, may range from approximately 1% to 30% by weight, with approximately 2% to 10% by weight being the preferred among and approximately 5% to 9% by weight being the most preferred amount.

In an optional but highly preferred embodiment, a dispersing agent which lowers the surface tension of water is incorporated into the film-forming compositions of the invention. The dispersing agent is constituted by an acid salt which functions to lower the surface tension of water in the compositions and illustrative acid salts which perform this function include the alkali metal and ammonium salts of ethylene diamine tetraacetic acid, nitrilo triaacetic acid, citric acid, phosphoric acid, tartaric acid, glycolic acid, malic acid, lactic acid, acetic acid and benzoic acid. It will be understood that other acid salts which function to lower the surface tension of water in the compositions may also be employed in the practice of the invention. Sodium salts of ethylene diamine tetraacetic acid represent the preferred dispersing agents for use in the practice of the invention. The dispersing agent is generally incorporated into the film-forming compositions in the form of aqueous solutions of such acid salts, such aqueous solutions being applied to the pigment-polymer blends as previously described and providing the amount of water to be added to the compositions as well as acting as the vehicle for the application of the dispersing agent to the pigment-polymer blends. Alternatively, but less preferably, the dispersing agent may be added in powder form to the pigment-polymer blend with the water being applied to the resulting blend of the three components in atomized form. The dispersing agent not only lowers the surface tension of the water in the film-forming compositions of the invention but also lowers the viscosity of the coating suspensions prepared from such compositions thereby providing smaller suspension droplets and smoother coatings for tablets and the like. While the invention may be practiced without the addition of a dispersing agent to the film-forming compositions, it has been found that theincorporation of a dispersing agent produces a better color development and quality of coating for tablets and the like.

The film-forming compositions of the invention are shelf-stable for extended periods of time without the use of preservatives and are not prone to settling or other breakdowns. Further, it is believed that such compositions remain free from bacteria formation such as may be normally caused by the solvent in liquid pigment dispersions.

To prepare coating suspensions for use in coating tablets and the like, the film-forming compositions of the invention are added to water and a plasticizer in accordance with conventional practice. The coating suspensions so prepared may be applied immediately to tablets without a waiting period such as overnight as is required with certain prior art systems. Any of the plasticizers known to the art such as polyethylene glycol 400, glycerin, propylene glycol, glycerine triacetate, triethyl citrate, tributyl citrate or diethyl phthalate may be used in formulating coating suspensions from the wet film-forming compositions of the invention.

In another, but less preferred, embodiment of the invention, a plasticizer may be incorporated into the wet film-forming compositions of the invention so that the resulting compositions may be simply added to water in order to form useful coating suspensions for coating tablets and the like.

In preparing the wet powder, edible, film-forming compositions of the invention, the proportions of pigment and polymer employed are not critical. In general, where the ratio of pigment to polymer is high, a flat appearing film of lower quality will be obtained whereas with lower ratios of pigment to polymer, a more glossy film finish and better film properties will be obtained. For acceptable results, the weight ratio of polymer to pigment should range between 1.5:1 and 3:1 with the ratio of approximately 2.5:1 being preferred where the pigment component is primarily constituted by a lake.

The proportion of dispersing agent incorporated into the film-forming compositions of the invention may vary widely but, in general, may constitute between 0.1 to 5.0% by weight based on the weight of the pigment and polymer components and more preferably between 0.5 to 2.0% by weight.

In another embodiment and in further accordance with the invention, it has also been unexpectedly found that useful wet powder, edible, clear film-forming compositions for coating tablets, capsules and the life with a clear coating may be formulated by applying water onto a film-forming, water-soluble or water-dispersible, edible, clear polymer in atomized form. Here again, when formulated in this manner, the resulting clear, film-forming compositions have been found capable of tolerating up to approximately 30% by weight water without forming fish eyes while yet remaining capable of forming a stable suspension upon dilution with additional water. Such clear, film-forming compositions prepared as described above and containing between approximately 1% and 30% by weight of water do not lump up or contain fish eyes and therefore require no long waiting period or pretreatment of the polymer component before being used to make coating compositions. When combined with additional water and a plasticizer, such clear, film-forming compositions yield a smooth, uniform coating composition for coating pharmaceutical tablets, capsules and the like with a clear coating. When a plasticizer is incorporated, water is first applied onto the polymer in atomized form following which the plasticizer is sprayed onto the resulting composition. Through this embodiment of the invention, it becomes possible to prepare smooth, clear, coating suspensions which can be used immediately or within 30 minutes for providing tablets, capsules or the like with a clear coating. In this embodiment of the invention, it is also optional, but preferable, for the clear, film-forming compositions to contain a dispersing agent constituted by an acid salt which lowers the surface tension of the water in the composition. Any of the dispersing agents enumerated above may be used in this embodiment of the invention.

In forming clear, film-forming compositions as above described, it is believed that the application of water onto the polymer advantageously preconditions the polymer as in the case of the pigment-polymer blend described above and avoids clumping or the formation of fish eyes either upon application of the water or when the resulting clear, film-forming compositions of the invention are added to water to form coating suspensions. Upon the application of water to a clear polymer as previously described, granules or an agglomeration of polymer particles are formed which unexpectedly go into solution readily in contrast to the addition of a polymer per se to water which tends to clump or form fish eyes. In forming clear, film-forming compositions of the invention in accordance with this additional embodiment, the same film-forming, water-soluble or water-dispersible, edible polymers, dispersing agents and plasticizers disclosed above may be employed, but the resulting compositions are clear because they contain no pigment component. Also, such clear, film-forming compositions can be prepared using a PK Blender or a Littleford FM 130 Blender which insure that the water is applied to the polymer in atomized form. The water may also be applied in atomized form by means of an aqueous solution of the dispersing agent where the latter is optionally but preferably incorporated into the film-forming compositions.

The following examples illustrate the practice of the invention.

EXAMPLE 1

The following ingredients were charged to a Littleford FM 130 blender:

| | |
|---|---|
| Hydroxypropylmethyl cellulose | 43 lb. |
| Titanium dioxide | 26 lb. |
| FD&C Yellow 6 Low dye lake | 1 lb. |

The ingredients were blended for two minutes to form a pigment-polymer blend. 3.5 lb. of a 10% aqueous sodium citrate solution was sprayed onto the pigment-polymer blend with mixing in approximately 2.5 minutes and then mixed for 1 minute after addition of the sodium citrate solution was complete. This effected application of the sodium citrate solution onto the pigment-polymer blend in atomized form. A dustless, free-flowing powdered film-forming composition was produced.

EXAMPLE 2

The following ingredients were charged to a Littleford W-10 mixer:

| | |
|---|---|
| Hydroxypropylmethyl cellulose | 1.36 kg. |
| Titanium dioxide | 0.35 kg. |
| FD&C Yellow 5 High dye lake | 0.20 kg. |
| FD&C Yellow 6 High dye lake | 0.03 kg. |

The ingredients were mixed for three minutes to form a pigment-polymer blend. 60 grams of a 10% aqueous solution of the tetrasodium salt of ethylene diamine tetraacetic acid was then sprayed onto the pigment-polymer blend in one minute, with mixing continued for one minute after the addition of the 10% solution was complete. A dustless, free-flowing powder was produced.

EXAMPLE 3

The following ingredients were charged to a PK Blender Model LBC-2P:

| | |
|---|---|
| Hydroxypropylmethyl cellulose | 400 g. |
| Titanium dioxide | 100 g. |
| FD&C Yellow 6 High dye lake | 100 g. |

The ingredients were mixed for four minutes to form a pigment-polymer blend. 60 grams of water was then sprayed onto the pigment-polymer blend in two minutes, with mixing continued for one minute after the addition of the water was complete. A dustless, free-flowing powder was produced.

EXAMPLE 4

Example 3 was repeated using 60 grams of a 10% aqueous solution of the tetrasodium salt of ethylene diamine tetraacetic acid in place of water. A dustless, free-flowing powder was produced.

EXAMPLE 5

Example 3 was repeated using 60 grams of a 10% aqueous solution of sodium citrate in place of water. A dustless, free-flowing powder was produced.

EXAMPLE 6

Example 3 was repeated using 30 grams of a 10% aqueous solution of sodium dibasic phosphate ($Na_2HPO_4$) in place of water. A dustless, free-flowing powder was produced.

EXAMPLE 7

Example 3 was repeated using FD&C Red 40 in place of FD&C Yellow 6 High dye lake. A dustless, free-flowing powder was produced.

EXAMPLE 8

Example 3 was repeated using FD&C Red 40 in place of FD&C Yellow 6 High dye lake and 30 grams of a 10% aqueous solution of the trisodium salt of ethylene diamine tetraacetic acid in place of water. A dustless, free-flowing powder was produced.

EXAMPLE 9

A coating suspension was prepared as follows: 87.5 grams of water and 1.5 grams of polyethylene glycol 400 were charged to a beaker. While stirring the beaker contents vigorously, 11 grams of the powder produced in Example 4 was added to the beaker. The powder readily dispersed and the suspension which formed thickened and became very smooth in 15 minutes.

The resulting coating suspension was applied immediately to tablets in a 4" Wurster Column, and a smooth glossy coating on the tablets was achieved in 15 minutes.

EXAMPLE 10

The following ingredients were charged to a PK Blender Model LBC-2P:

| | |
|---|---|
| Hydroxypropylmethyl cellulose | 360 g. |
| Maltrin M-100 (Maltodextrin) | 240 g. |

The above polymer ingredients should preferably be distributed equally in each shell of the blender and should be ½ to +e,fra 3+ee the way up the intensifier bar of the blender. The blender was closed and mixing of the dry blend was carried out for 4 to 5 minutes with both the shell and intensifier bar mixing being used. After the polymer ingredients were thus blended, mixing with both the shell and intensifier bar was continued and the liquid feed pump was turned on. 38 grams of a 10% aqueous solution of sodium citrate was fed onto the polymer blend in atomized form followed by the addition of 48 grams of polyethylene glycol 400 as a plasticizer. After the addition of the sodium citrate solution and plasticizer, the liquid feed pump was allowed to run for 1 minute to clear the lines. After the liquid feed pump was shut off, the shell and intensifier bar were allowed to mix for 30 seconds and the blender was shut off. A dustless, free-flowing powder was produced.

EXAMPLE 11

The composition of Example 10 was used to make a coating solution. 863.2 grams of water were added to a container equipped with a variable speed mixer. The mixer was started and once a vortex was formed, 136.8 grams of the composition of Example 10 was added in a steady and consistent manner. The speed of the mixer was increased as the solution became more viscous, with the composition being added to the center of the vortex for best mixing. After the complete addition of the Example 10 composition, the speed of the mixer was reduced to reduce aeration of the solution. The sides of the container were scraped to remove any clumps which were added to the center of the solution. Mixing was continued for 30 minutes to produce a smooth, clear coating solution.

EXAMPLE 12

The clear, coating solution of Example 11 was used to coat tablets by column or pan coating. The coating solution of Example 11 was charged to the liquid feed system and the tablets to be coated were charged to the coating equipment. The tablets were warmed and the coating solution was sprayed onto the tablets. The resulting tablets had a smooth, clear, glossy coating.

EXAMPLE 13

The procedure of Example 10 was generally followed to produce a wet powder, edible, clear, film-forming composition having the following composition:

| Component | Wt. % |
| --- | --- |
| Hydroxypropylmethyl cellulose | 68.2 |
| Hydroxypropyl cellulose | 22.8 |
| Water | 9.0 |

A dustless, free-flowing powder was produced.

EXAMPLE 14

The procedure of Example 10 was generally followed to produce a wet powder, edible, clear, film-forming composition having the following composition:

| Component | Wt. % |
| --- | --- |
| Hydroxypropylmethyl cellulose | 94.6 |
| Sodium citrate | 0.4 |
| Water | 5.0 |

A dustless, free-flowing powder was produced.

EXAMPLE 15

The procedure of Example 10 was generally followed to produce a wet powder, edible, clear, film-forming composition having the following composition:

| Component | Wt. % |
| --- | --- |
| Hydroxypropylmethyl cellulose | 91.5 |
| Sodium citrate | 0.4 |
| Water | 8.1 |

EXAMPLE 16

A dustless, free-flowing powder was produced.
The procedure of Example 10 was generally followed to produce a wet powder, edible, clear, film-forming composition having the following composition:

| Component | Wt. % |
| --- | --- |
| Hydroxypropylmethyl cellulose | 84.0 |
| Sodium citrate | 1.0 |
| Talc | 5.0 |
| Glycerin triacetate | 5.0 |
| Water | 5.0 |

A dustless, free-flowing powder was produced.

EXAMPLE 17

The procedure of Example 10 was generally followed to produce a wet powder, edible, clear, film-forming composition having the following composition:

| Component | Wt. % |
| --- | --- |
| Hydroxypropylmethyl cellulose | 87.70 |
| Sodium citrate | 0.14 |
| Talc | 3.90 |
| Glycerin triacetate | 4.30 |
| Water | 3.90 |

A dustless, free-flowing powder was produced.

EXAMPLE 18

The procedure of Example 10 was generally followed to produce a wet powder, edible, clear, film-forming composition having the following composition:

| Component | Wt. % |
| --- | --- |
| Hydroxypropylmethyl cellulose | 90.3 |
| Tetrasodium ethylene diamine tetraacetate | 0.5 |
| Polyethylene glycol | 4.5 |
| Water | 4.7 |

A dustless, free-flowing powder was produced.

EXAMPLE 19

The procedure of Example 10 was generally followed to produce a wet powder, edible, clear, film-forming composition having the following composition:

| Component | Wt. % |
| --- | --- |
| Hydroxypropylmethyl cellulose | 85.4 |
| Tetrasodium ethylene diamine tetraacetate | 0.5 |
| Polyethylene glycol | 4.3 |
| Water | 4.6 |

A dustless, free-flowing powder was produced.

EXAMPLE 20

The procedure of Example 10 was generally followed to produce a wet powder, edible, clear, film-forming composition having the following composition:

| Component | Wt. % |
| --- | --- |
| Hydroxypropylmethyl cellulose | 91.5 |
| Triethyl citrate | 4.6 |
| Water | 3.8 |

A dustless, free-flowing powder was produced.

EXAMPLE 21

The procedure of Example 10 was generally followed to produce a wet powder, edible, clear, film-forming composition having the following composition:

| Component | Wt. % |
| --- | --- |
| Hydroxypropylmethyl cellulose | 84.50 |
| Sodium citrate | 0.35 |
| Glycerine triacetate | 8.50 |
| Talc | 3.50 |
| Water | 3.20 |

A dustless, free-flowing powder was produced.

EXAMPLE 22

The procedure of Example 10 was generally followed to produce a wet powder, edible, clear, film-forming composition having the following composition:

| Component | Wt. % |
| --- | --- |
| Hydroxypropylmethyl cellulose | 84.50 |
| Sodium citrate | 0.35 |
| Glycerin triacetate | 8.00 |
| Talc | 4.00 |
| Water | 3.20 |

A dustless, free-flowing powder was produced.

EXAMPLE 23

The procedure of Example 10 was generally followed to produce a wet powder, edible, clear, film-forming composition having the following composition:

| Component | Wt. % |
| --- | --- |
| Hydroxypropylmethyl cellulose | 85.50 |
| Sodium citrate | 0.35 |
| Glycerin triacetate | 6.00 |
| Talc | 5.00 |
| Water | 3.20 |

A dustless, free-flowing powder was produced.

EXAMPLE 24

The procedure of Example 10 was generally followed to produce a wet powder, edible, clear, film-forming composition having the following composition:

| Component | Wt. % |
| --- | --- |
| Hydroxypropylmethyl cellulose | 78.70 |
| Sodium citrate | 0.55 |
| Polyvinyl pyrrolidone | 15.70 |
| Water | 5.00 |

A dustless, free-flowing powder was produced.

EXAMPLE 25

The procedure of Example 10 was generally followed to produce a wet powder, edible, clear, film-forming composition having the following composition:

| Component | Wt. % |
| --- | --- |
| Hydroxypropylmethyl cellulose | 90.20 |
| Tetrasodium ethylene diamine tetraacetate | 0.53 |
| Polyethylene glycol | 4.50 |
| Water | 4.70 |

A dustless, free-flowing powder was produced.

EXAMPLE 26

The procedure of Example 10 was generally followed to produce a wet powder, edible, clear, film-forming composition having the following composition:

| Component | Wt. % |
| --- | --- |
| Hydroxypropylmethyl cellulose | 95.0 |
| Water | 5.0 |

A dustless, free-flowing powder was produced.

EXAMPLE 27

The procedure of Example 10 was generally followed to produce a wet powder, edible, clear, film-forming composition having the following composition:

| Component | Wt. % |
| --- | --- |
| Hydroxypropylmethyl cellulose | 90.0 |
| Sodium citrate | 0.4 |
| Polyethylene glycol | 6.0 |
| Water | 3.6 |

A dustless, free-flowing powder was produced.

EXAMPLE 28

The procedure of Example 10 was generally followed to produce a wet powder, edible, clear, film-forming composition having the following composition:

| Component | Wt. % |
| --- | --- |
| Hydroxypropylmethyl cellulose | 45.75 |
| Modified starch ("Purity Gum 59", National Starch) | 45.75 |
| Sodium citrate | 0.50 |
| Water | 8.00 |

A dustless, free-flowing powder was produced.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A wet powder, edible, clear, film-forming composition for use in coating tablets and capsules with a clear coating comprising a clear, film-forming, water soluble or water-dispersible, edible polymer and between approximately 1% and approximately 30% by weight of water, said composition being formed by applying water onto said polymer in atomized form and said composition being capable of forming a stable suspension upon dilution with additional water without the formation of fish eyes.

2. The wet powder, edible, clear, film-forming composition as set forth in claim 1 wherein said polymer is selected from the group consisting of methyl cellulose, hydroxypropylmethyl cellulose, hydroxypropyl cellulose, polyvinyl pyrrolidone, maltodextrin, polydextrose, modified starches and a natural gum selected from the group consisting of gum tragacanth, gum acacia and a xanthan gum.

3. The wet powder, edible, clear, film-forming composition as set forth in claim 1 wherein said polymer is hydroxypropylmethyl cellulose.

4. The wet powder, edible, clear, film-forming composition as set forth in claim 1 wherein said composition contains from approximately 2% to 10% by weight of water.

5. The wet powder, edible, clear, film-forming composition as set forth in claim 1 wherein said composition contains from approximately 5% to 9% by weight of water.

6. The wet powder, edible, clear, film-forming composition as set forth in claim 1 wherein said composition additionally includes a plasticizer.

7. A wet powder, edible, clear, film-forming composition for use in coating tablets and capsules with a clear coating comprising a clear, film-forming, water soluble or water-dispersible, edible polymer, between approximately 1% and approximately 30% by weight of water, and a dispersing agent constituted by an acid salt which lowers the surface tension of water in the composition, said composition being formed by applying an aqueous solution of said dispersing agent onto said polymer in atomized form and said composition being capable of forming a stable suspension upon dilution with additional water without the formation of fish eyes.

8. A wet powder, edible, clear, film-forming composition as set forth in claim 7 wherein said acid salt is selected from the group consisting of the alkali metal and ammonium salts of ethylene diamine tetraacetic acid, nitrilo triacetic acid, citric acid, phosphoric acid, tartaric acid, glycolic acid, malic acid, lactic acid, acetic acid and benzoic acid.

9. The wet powder, edible, clear, film-forming composition as set forth in claim 7 wherein said acid salt is an alkali metal or ammonium salt of ethylene diamine tetraacetic acid.

10. The wet powder, edible, clear, film-forming composition as set forth in claim 7 wherein said polymer is selected from the group consisting of methyl cellulose, hydroxypropylmethyl cellulose, hydroxypropyl cellulose, polyvinyl pyrrolidone, maltodextrin, polydextrose, modified starches and a natural gum selected from the group consisting of gum tragacanth, gum acacia and a xanthan gum.

11. The wet powder, edible, clear, film-forming composition as set forth in claim 7 wherein said polymer is hydroxypropylmethyl cellulose.

12. The wet powder, edible, clear, film-forming composition as set forth in claim 7 wherein said composition contains from approximately 2% to 10% by weight of water.

13. The wet powder, edible, clear, film-forming composition as set forth in claim 7 wherein said composition contains from approximately 5% to 9% by weight of water.

14. The wet powder, edible, clear, film-forming composition as set forth in claim 7 wherein said composition additionally includes a plasticizer.

* * * * *

UNITED STATES PATENT AND TRADEMARK OFFICE
CERTIFICATE OF CORRECTION

PATENT NO. : 5,591,455
DATED : January 7, 1997
INVENTOR(S) : Signorino

It is certified that error appears in the above-indentified patent and that said Letters Patent is hereby corrected as shown below:

Column 8, line 25, delete "+e,fra 3+ee " and substitute therefor --3/4--

Column 9, line 43, move entire sentence to line 39 such that "A dustless, free-flowing powder was produced." is the last line of Example 15"

Signed and Sealed this

Sixteenth Day of September, 1997

Attest:

BRUCE LEHMAN

Attesting Officer

Commissioner of Patents and Trademarks